United States Patent
Mandalia et al.

(10) Patent No.: US 11,705,227 B2
(45) Date of Patent: Jul. 18, 2023

(54) INTERNET OF THINGS COMMUNICATION AND SOCIAL NETWORK FOR MEDICINE DISPOSITION IN HOSPITALS

(71) Applicant: KYNDRYL, INC., New York, NY (US)

(72) Inventors: Baiju Dhirajlal Mandalia, Boca Raton, FL (US); Harish Rajagopal, Holsworthy (AU); Pravin Bernard Phadte, Bangalore (IN); Joseph Dawson Davis, III, Roanoke, TX (US); Joseph David Robinson, Cary, NC (US); John F. Hollingsworth, Wynnewood, PA (US)

(73) Assignee: Kyndryl, Inc., New York, NY (US)

( * ) Notice: Subject to any disclaimer, the term of this patent is extended or adjusted under 35 U.S.C. 154(b) by 351 days.

(21) Appl. No.: 16/894,300

(22) Filed: Jun. 5, 2020

(65) Prior Publication Data

US 2021/0383901 A1     Dec. 9, 2021

(51) Int. Cl.

| G16H 10/60 | (2018.01) |
|---|---|
| G16H 40/60 | (2018.01) |
| H04W 4/80 | (2018.01) |
| G06F 1/16 | (2006.01) |
| G16H 50/70 | (2018.01) |

(52) U.S. Cl.
CPC ............. *G16H 10/60* (2018.01); *G06F 1/163* (2013.01); *G16H 40/60* (2018.01); *G16H 50/70* (2018.01); *H04W 4/80* (2018.02)

(58) Field of Classification Search
CPC ........ G16H 10/60; G16H 40/60; G16H 50/70; G16H 20/13; G16H 40/20; G16H 50/20; G06F 1/163; H04W 4/80
See application file for complete search history.

(56) References Cited

U.S. PATENT DOCUMENTS

| 6,539,281 B2 * | 3/2003 | Wan ................... G07F 17/0092 |
|---|---|---|
| | | 700/244 |
| 9,427,520 B2 * | 8/2016 | Batch ..................... G16H 40/67 |
| 9,747,743 B2 * | 8/2017 | Brown ................... G07F 11/62 |

(Continued)

OTHER PUBLICATIONS

Jara et al.,"Drug Identification and Interaction Checker based on IoT to Minimize Adverse Drug Reactions and Improve Drug Compliance", vol. 18, ACM, Jan. 2018, 13 pages.

(Continued)

*Primary Examiner* — Eliza A Lam
(74) *Attorney, Agent, or Firm* — Erik Swanson; Andrew M. Calderon; Calderon Safran & Cole, P.C.

(57) ABSTRACT

Methods and systems for medicine disposition in hospitals are disclosed. A method includes: receiving, by a computing device, an electronic health record (EHR) of a patient; receiving, by the computing device, an order to dispense a medicine to the patient; receiving, by the computing device, information from a wearable device of the patient and updating the EHR of the patient based on the information from the wearable device of the patient; determining, by the computing device, that a health concern is not identified based on the information from the wearable device of the patient; and dispensing, by the computing device, the medicine to the patient in accordance with the order.

20 Claims, 3 Drawing Sheets

(56) References Cited

U.S. PATENT DOCUMENTS

| | | | | |
|---|---|---|---|---|
| 2008/0004904 | A1* | 1/2008 | Tran | A61B 5/411 |
| | | | | 340/286.07 |
| 2011/0166891 | A1 | 7/2011 | Zerhusen et al. | |
| 2013/0304482 | A1* | 11/2013 | Siddiqui | G16H 10/60 |
| | | | | 705/2 |
| 2014/0244768 | A1 | 8/2014 | Shuman et al. | |
| 2017/0124839 | A1* | 5/2017 | Weissman | G08B 25/08 |
| 2017/0255760 | A1 | 9/2017 | Lee et al. | |
| 2017/0351838 | A1* | 12/2017 | Chen | G16H 20/10 |
| 2018/0308569 | A1 | 10/2018 | Luellen | |

OTHER PUBLICATIONS

Shelke et al.,"Internet of Medical Things", Technology Intelligence & IP Research. Aranca 2016. 20 pages.

Anonymous, "Fast Healthcare Interoperability Resources" https://en.wikipedia.org/wiki/Fast_Healthcare_Interoperability_Resources, downloaded Jun. 5, 2020, 5 pages.

* cited by examiner

INTERNET OF THINGS COMMUNICATION AND SOCIAL NETWORK FOR MEDICINE DISPOSITION IN HOSPITALS

BACKGROUND

Aspects of the present disclosure generally relate to computing devices and, more particularly, to methods and systems for medicine disposition in hospitals.

Hospitals rely on accurate records and an understanding of a patient's condition to ensure accurate medicine disposition to a patient. Allergy bands may be used to identify a patient's allergies (e.g., to particular medicines). Printed lists may be used to indicate particular medicines to be rendered to a patient. Radio frequency identification (RFID) tags on medicine bottles may be used to identify particular medicines contained therein.

An electronic health record (EHR) is a digital record of a patient's medical and treatment history. An EHR may include clinical data collected by a healthcare provider. An EHR may include a patient's medical history, diagnoses, medicines, treatment plans, immunization dates, allergies, radiology images, and/or laboratory and test results. An EHR system securely stores EHRs for plural patients and may facilitate access to the EHRs by multiple authorized providers across one or more healthcare organizations (e.g., primary care doctors' offices, specialist doctors' offices, hospitals, etc.).

Internet of Things (IoT) devices include Internet and/or network-connected devices (e.g., home and building automation (smart home) devices/appliances, sensors, sensor networks, control systems, etc.

SUMMARY

In a first aspect of the disclosure, there is a method that includes: receiving, by a computing device, an electronic health record (EHR) of a patient; receiving, by the computing device, an order to dispense a medicine to the patient; receiving, by the computing device, information from a wearable device of the patient and updating the EHR of the patient based on the information from the wearable device of the patient; determining, by the computing device, that a health concern is not identified based on the information from the wearable device of the patient; and dispensing, by the computing device, the medicine to the patient in accordance with the order.

In another aspect of the disclosure, there is a computer program product that includes one or more computer readable storage media having program instructions collectively stored on the one or more computer readable storage media. The program instructions are executable to: receive an electronic health record (EHR) of a patient; receive an order to dispense a medicine to the patient; receive information from a wearable device of the patient and update the EHR of the patient based on the information from the wearable device of the patient; determine that a health concern is not identified based on the information from the wearable device of the patient; receive data from a digital video camera and determine a current health status of the patient based on the data from the digital video camera; and update the EHR of the patient based on the determined current health status of the patient.

In another aspect of the disclosure, there is a system that includes: a processor, a computer readable memory, one or more computer readable storage media, and program instructions collectively stored on the one or more computer readable storage media. The program instructions are executable to: receive an electronic health record (EHR) of a patient; receive an order to dispense a medicine to the patient; receive information from a wearable device of the patient and update the EHR of the patient based on the information from the wearable device of the patient; determine that a health concern is not identified based on the information from the wearable device of the patient; and dispense the medicine to the patient in accordance with the order.

BRIEF DESCRIPTION OF THE DRAWINGS

Aspects of the present disclosure are described in the detailed description which follows, in reference to the noted plurality of drawings by way of non-limiting examples of exemplary embodiments of the present disclosure.

DETAILED DESCRIPTION

Figure 1:
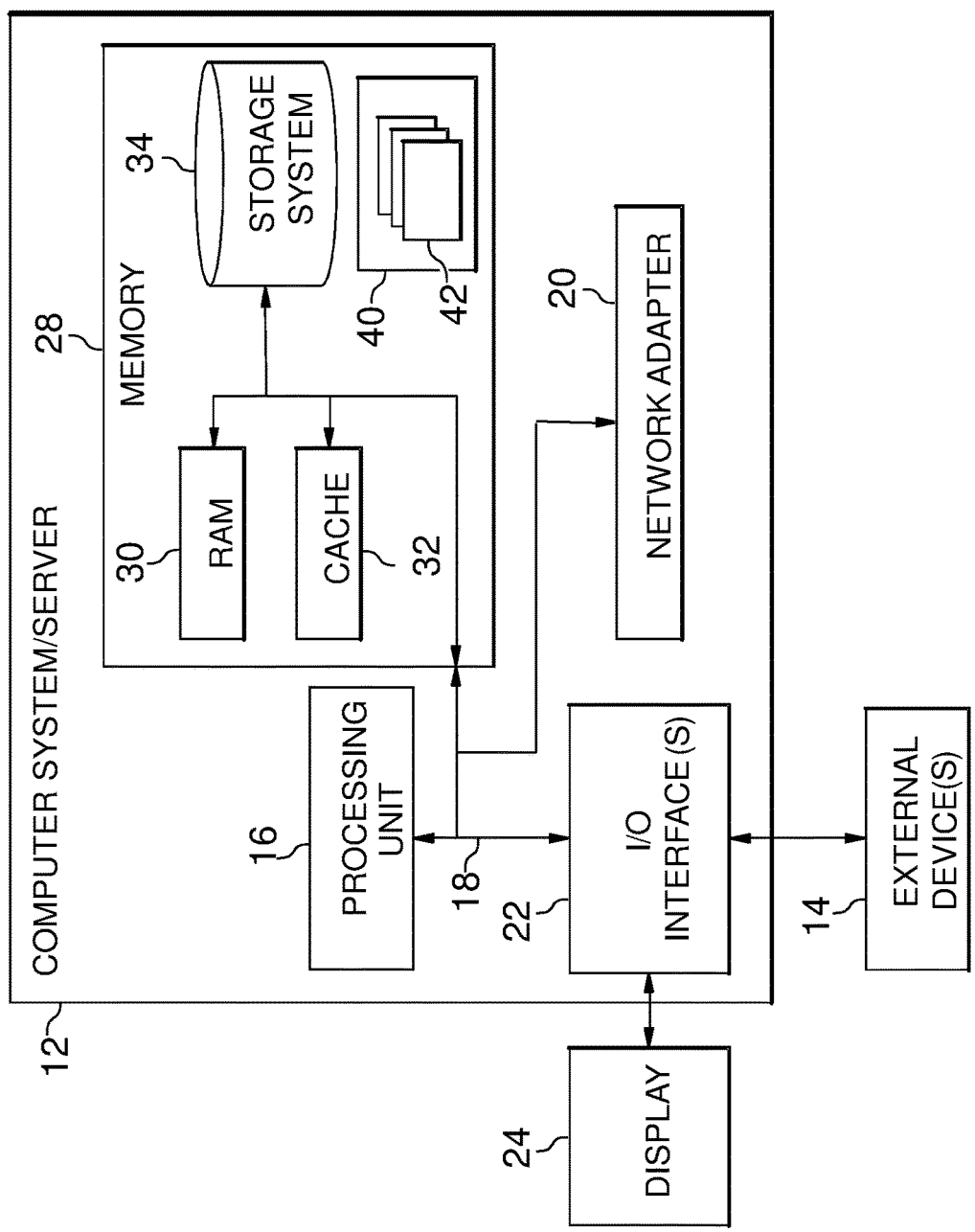
FIG. 1 depicts a computer system in accordance with aspects of the disclosure.

Aspects of the present disclosure generally relate to computing devices and, more particularly, to methods and systems for medicine disposition in hospitals. As described herein, aspects of the disclosure include a method and system that incorporate dynamic real time error protection mechanisms for medicine disposition. In embodiments, a prescription and a state of a patient is recorded in real-time with an EHR. In embodiments, in a hospital, a pharmacy dispatches medicine for different patients on an intelligent medical cart with intelligent medicine bottles that are dynamically checked by an verification device at each patient's room to validate and inspect the medicine. In embodiments, a method and system provide for real-time consolidation and communication of available information from multiple databases attached to IoT devices that update the EHR and provide real-time notifications at the point of delivery to alert nurses and doctors to avoidable interactions related to known counter-indicated medical treatments based on existing medical databases and including updated information gathered from a patient by measurement of body functions (e.g., pulse rate, blood pressure, body temperature, respiration rate, etc.) and or diagnostic testing (e.g., blood tests).

Conventional methods for medicine disposition in hospitals (e.g., a printed list of medicines to be administered, allergy bands on patients, and RFID tags on medicine bottles) may risk errors due to complex treatment situations, general miscommunications, incomplete or inaccurate records, and/or staff workload. Embodiments address these problems with by providing methods and systems for medicine disposition in hospitals. In particular, embodiments improve the technology of EHR systems by providing methods and systems that use dynamic and real-time measurements to understand a patient's current state and update a patient's EHR before dispensing any medicine. Accordingly, through the use of rules that can improve computer-related technology, implementations of the disclosure allow computer performance of functions not previously performable by a computer. Additionally, implementations of the disclosure use techniques that are, by definition, rooted in computer technology (e.g., IoT devices, EHRs, etc.). It is to be understood that the aforementioned advantages, as well as other advantages described herein, are example advantages and should not be construed as limiting. Embodiments of the present disclosure can contain all, some, or none of the advantages while remaining within the spirit and scope of the present disclosure.

In embodiments, a method and system check for medicine allergies, medicines with interactions, medicines which adversely react with a patient, a patient's current real-time symptoms and reactions, blood pressure, blood sugar changes, incorrect medicine (e.g., based on a comparison of size, shape, and color of a pill to an expected size, shape, and color), and/or incorrect dosage (e.g., based on weight or a comparison of size, shape, and color of a pill to an expected size, shape, and color) prior to dispensing a dose of medicine to a patient. Additionally, in embodiments, a method and system update a patient's EHR in real-time with a patient's diagnostic testing results (e.g., blood test results and/or results of analysis of cerebrospinal fluid, synovial fluid, gastric fluids, etc.). Additionally, in embodiments, a method and system update a patient's EHR in real-time with a measurements of a patient's body functions, including electrical activity of the heart with electrocardiography (ECG) and/or electrical activity of the brain with electroencephalography (EEG).

In embodiments, a method and system provide a multifaceted error-protection scheme for medicine disposition. Additionally, in embodiments, a method and system are provided that enhance patient-nurse communication, including by performing cognitive analysis of patient complaints (e.g., adverse reactions to a prior dose of a medicine).

In embodiments, an verification device acts as a real-time firewall working in conjunction with EHR data to prevent medicine dispensation errors. In particular, embodiments leverage an EHR system that utilizes blockchain or other techniques to ensure security, reliability, and tamper-proofing of the EHRs stored in the EHR system. Additionally, embodiments utilize visual recognition capabilities to determine a condition of a patient and to confirm that a correct medicine is being dispensed. In embodiments, a method and system receive, in real time, a patient's current vitals and/or allergy warnings from wearable IoT devices and/or an IoT hospital bed, and the patient's EHR in an EHR system is then updated with this information. In embodiments, an intelligent medical cart is provided that receives communications from intelligent medicine bottles, e.g., via RFID and/or Bluetooth. In embodiments, a hospital bed, a medical cart, a wearable device, and a robot are all part of an IoT social network that creates a real-time firewall to prevent medicine errors, as described herein, e.g., with respect to FIG. 3.

In embodiments, an internet of things system incorporating dynamic real time error protection mechanisms for medicine disposition includes: recording a prescription and a state of a patient in real-time in an EHR; dispatching, from a pharmacy in a hospital, medicine for different patients on an intelligent cart with intelligent medicine bottles that are dynamically checked by an verification device at each patient's side to validate and inspect the medicine; and consolidating and communicating the available information from multiple databases attached to IoT devices, updating the EHR, and providing real time notifications at the point of delivery to alert nurses and doctors of avoidable interactions related to known counter-indicated medical treatments based on existing medical databases, including updated information gathered from diagnostic testing, measurement of body functions, etc.

To the extent the implementations collect, store, or employ personal information of individuals, it should be understood that such information shall be used in accordance with all applicable laws concerning protection of personal information. Additionally, the collection, storage, and use of such information may be subject to advance notification and consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium or media, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
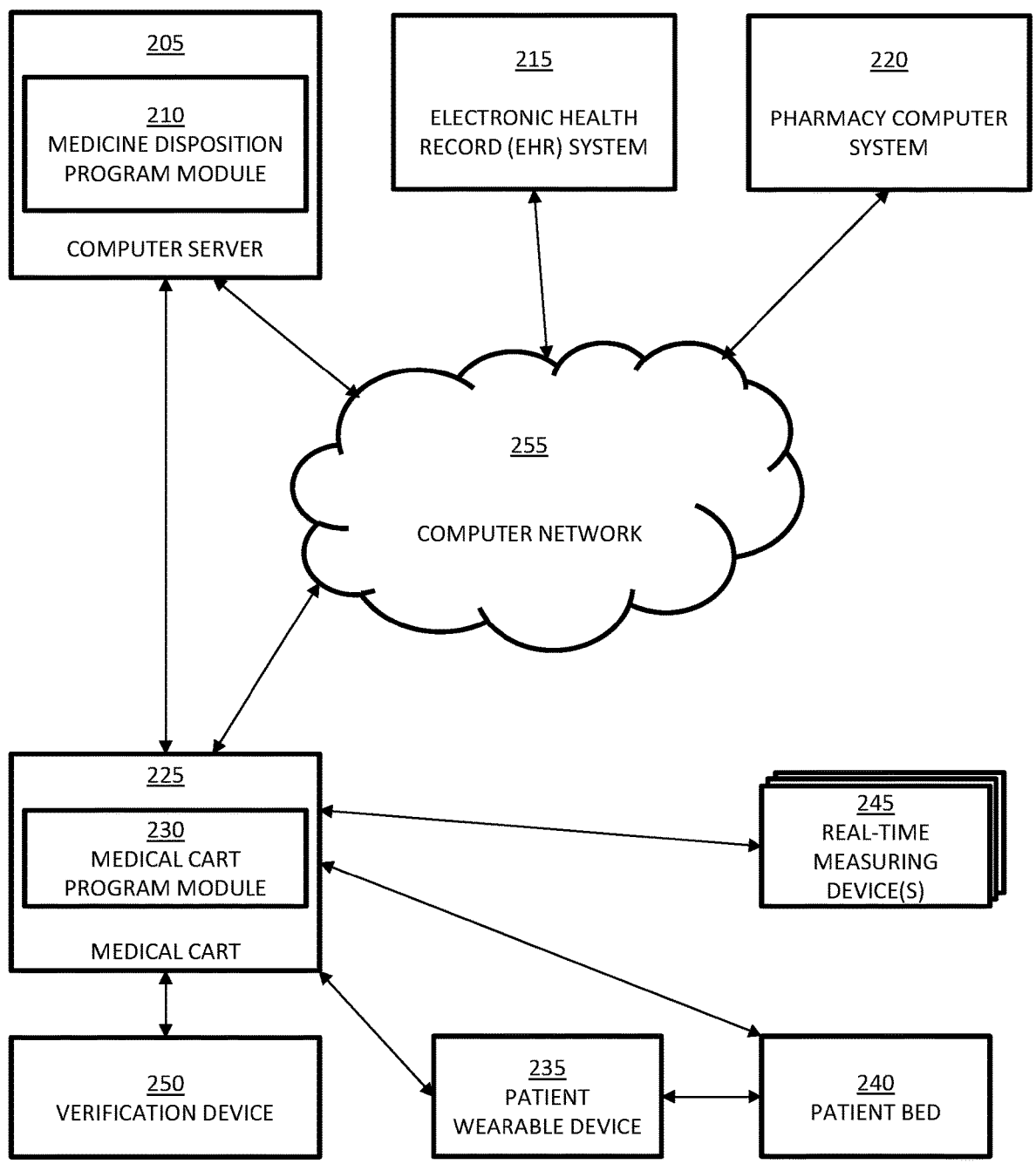
FIG. 2 depicts an illustrative environment in accordance with aspects of the disclosure.

FIG. 2 depicts an illustrative environment 200 in accordance with aspects of the disclosure. As shown, the environment 200 comprises a computer server 205, an electronic health record (EHR) system 215, a pharmacy computer system 220, a medical cart 225, a patient wearable device 235, a patient bed 240, at least one real-time measuring device 245, and a verification device 250 which are in communication via a computer network 255. In embodiments, the computer network 255 is any suitable network including any combination of a LAN, WAN, or the Internet.

The quantity of devices and/or networks in the environment 200 is not limited to what is shown in FIG. 2. In practice, the environment 200 may include additional devices and/or networks; fewer devices and/or networks; different devices and/or networks; or differently arranged devices and/or networks than illustrated in FIG. 2. Also, in some implementations, one or more of the devices of the environment 200 may perform one or more functions described as being performed by another one or more of the devices of the environment 200.

In embodiments, the computer server 205 is a computer device comprising one or more elements of the computer system/server 12 (as shown in FIG. 1). In other embodiments, the computer server 205 is implemented as hardware and/or software using components such as mainframes; RISC (Reduced Instruction Set Computer) architecture based servers; servers; blade servers; storage devices; networks and networking components; virtual servers; virtual storage; virtual networks, including virtual private networks; virtual applications and operating systems; and/or virtual clients.

In embodiments, the computer server 205 includes a medicine disposition program module 210, which comprises one or more of the program modules 42 shown in FIG. 1. In embodiments, the medicine disposition program module 210 includes program instructions that incorporate dynamic real-time error protection mechanisms for medicine disposition. In embodiments, the medicine disposition program module 210 stores profiles for each of the pharmacy computer system 220, medical cart 225, patient wearable device 235, patient bed 240, real-time measuring devices 245, and verification device 250. In embodiments, the profiles include information describing each of the pharmacy computer system 220, medical cart 225, patient wearable device 235, patient bed 240, real-time measuring devices 245, and verification device 250 and that is used to verify the integrity and consistency of data received therefrom. In embodiments, the program instructions included in the medicine disposition program module 210 of the computer server 205 are executed by one or more hardware processors. In other embodiments, the functionality of the medicine disposition program module 210 is instead provided by the medical cart program module 230 of the medical cart 225.

Still referring to FIG. 2, in embodiments, the EHR system 215 is a computer device comprising one or more elements of the computer system/server 12 (as shown in FIG. 1). In other embodiments, the EHR system 215 is implemented as hardware and/or software using components such as mainframes; RISC (Reduced Instruction Set Computer) architecture based servers; servers; blade servers; storage devices; networks and networking components; virtual servers; virtual storage; virtual networks, including virtual private networks; virtual applications and operating systems; and/or virtual clients.

In embodiments, the EHR system 215 includes EHR software that maintains plural EHRs, each EHR corresponding to a particular patient. The EHR system 215 provides secure storage of the plural EHRs and secure access to the EHRs by one or more authorized providers at one or more healthcare organizations, including functionality for creating and updating the EHRs. In embodiments, a messaging protocol used for communication between the EHR system 215 and other devices in the environment 200 is the standard FHIR® (Fast Healthcare Interoperability Resources) RESTful (representational state transfer) API (Application Programming Interface), defined by HL7® (FHIR and HL7 are registered trademarks of Health Level Seven International, Inc.).

Still referring to FIG. 2, in embodiments, the pharmacy computer system 220 is a computer device comprising one or more elements of the computer system/server 12 (as shown in FIG. 1). In other embodiments, the pharmacy computer system 220 is implemented as hardware and/or software using components such as mainframes; RISC (Reduced Instruction Set Computer) architecture based servers; servers; blade servers; storage devices; networks and networking components; virtual servers; virtual storage; virtual networks, including virtual private networks; virtual applications and operating systems; and/or virtual clients.

In embodiments, the pharmacy computer system 220 includes pharmacy software that manages medicine records in the hospital, including prescriptions written by healthcare providers for patients. In embodiments, the pharmacy computer system 220 receives prescriptions in electronic form from healthcare providers, stores prescription history for patients, and stores drug allergy information for patients. In embodiments, the pharmacy computer system 220 is used by pharmacists to retrieve prescription orders for fulfillment. Additionally, in embodiments, the pharmacy computer system 220 provides information about prescriptions to the medical cart program module 230 of the medical cart 235.

Still referring to FIG. 2, in embodiments, the medical cart 225 is an intelligent mobile cart that holds medicine to be delivered to one or more patients at a healthcare organization (e.g., at a hospital). In embodiments, the medical cart 225 is a self-driving robotic cart that is able to autonomously or semi-autonomously navigate between a pharmacy in a hospital and patient rooms in the hospital. In other embodiments, the self-driving functionality is omitted from the medical cart 225. In embodiments, the medical cart 225 includes a computer device comprising one or more elements of the computer system/server 12 (as shown in FIG. 1).

In embodiments, the medical cart 225 includes a medical cart program module 230, which comprises one or more of the program modules 42 shown in FIG. 1. In embodiments, the medical cart program module 230 includes program instructions that communicate with the medicine disposition program module 210 of the computer server 205, the EHR system 215, and/or the pharmacy computer system 220 to receive information about prescriptions and patients, read from and write to EHRs, provide real-time notifications at the point of delivery to alert nurses and doctors, and receive information from doctors and nurses. In embodiments, the medical cart program module 230 creates and/or maintains a virtual database that includes information about medicine for patients in the hospital. In embodiments, the program instructions included in the medical cart program module 225 of the medical cart 225 are executed by one or more hardware processors.

Still referring to FIG. 2, in embodiments, the patient wearable device 235 is any type of mobile device, mobile telephone, computer-based activity tracker, fitness tracker, smart watch, sleep tracker, biosensor device, or other device that is typically carried or worn by a patient and that tracks information related to activity, fitness, location, and/or health. In embodiments, the patient wearable device 235 is used by a patient to synchronize medical records (including drug allergy information) and medicines with the medical cart 225. In embodiments, the patient wearable device 235 communicates with the medical cart program module 230 of the medical cart 225. In embodiments, the patient wearable device 235 includes one or more elements of the computer system/server 12 (as shown in FIG. 1). In embodiment, the patient wearable device 235 includes one or more sensors that collect biometric data (e.g., heart rate) and/or data that is related to activity, fitness, location, and/or health.

Still referring to FIG. 2, in embodiments, the patient bed 240 is a hospital bed that is an IoT device that includes one or more sensors such as digital video cameras, digital still cameras, microphones, temperature sensors, motion sensors, location sensors, and any other type of digital sensor that collects data about a patient using the patient bed 240 and/or an environment (e.g., a hospital room) in which the patient bed 240 is located. In embodiments, the patient bed 240 communicates with the medical cart 225 and/or the patient wearable device 235. In embodiments, the patient bed 240 includes one or more elements of the computer system/server 12 (as shown in FIG. 1).

Still referring to FIG. 2, in embodiments, each of the real-time measuring devices 245 is an IoT portable medical device that measures current medical characteristics of a patient (e.g., pulse, blood pressure, blood oxygen saturation, respiration rate, etc.). In embodiments, each of the real-time measuring devices 245 communicates with the medical cart 225. In embodiments, each of the real-time measuring devices 245 includes one or more elements of the computer system/server 12 (as shown in FIG. 1).

Still referring to FIG. 2, in embodiments, the verification device 250 includes one or more elements of the computer system/server 12 (as shown in FIG. 1). In embodiments, the verification device 250 is an IoT device that is a mobile or stationary robot that includes one or more sensors such as digital video cameras, digital still cameras, microphones, temperature sensors, motion sensors, location sensors, and any other type of digital sensor that collects data about a patient and/or an environment (e.g., a hospital room) in which the patient is located. In embodiments, the verification device 250 communicates with the medical cart 225 and provides visual verification of a medicine to be dispensed by the medical cart 225. In embodiments, the verification device 250 sends alerts to doctors and/or nurses regarding when there may be a problem associated with dispensing a medicine to a patient.

Figure 3:
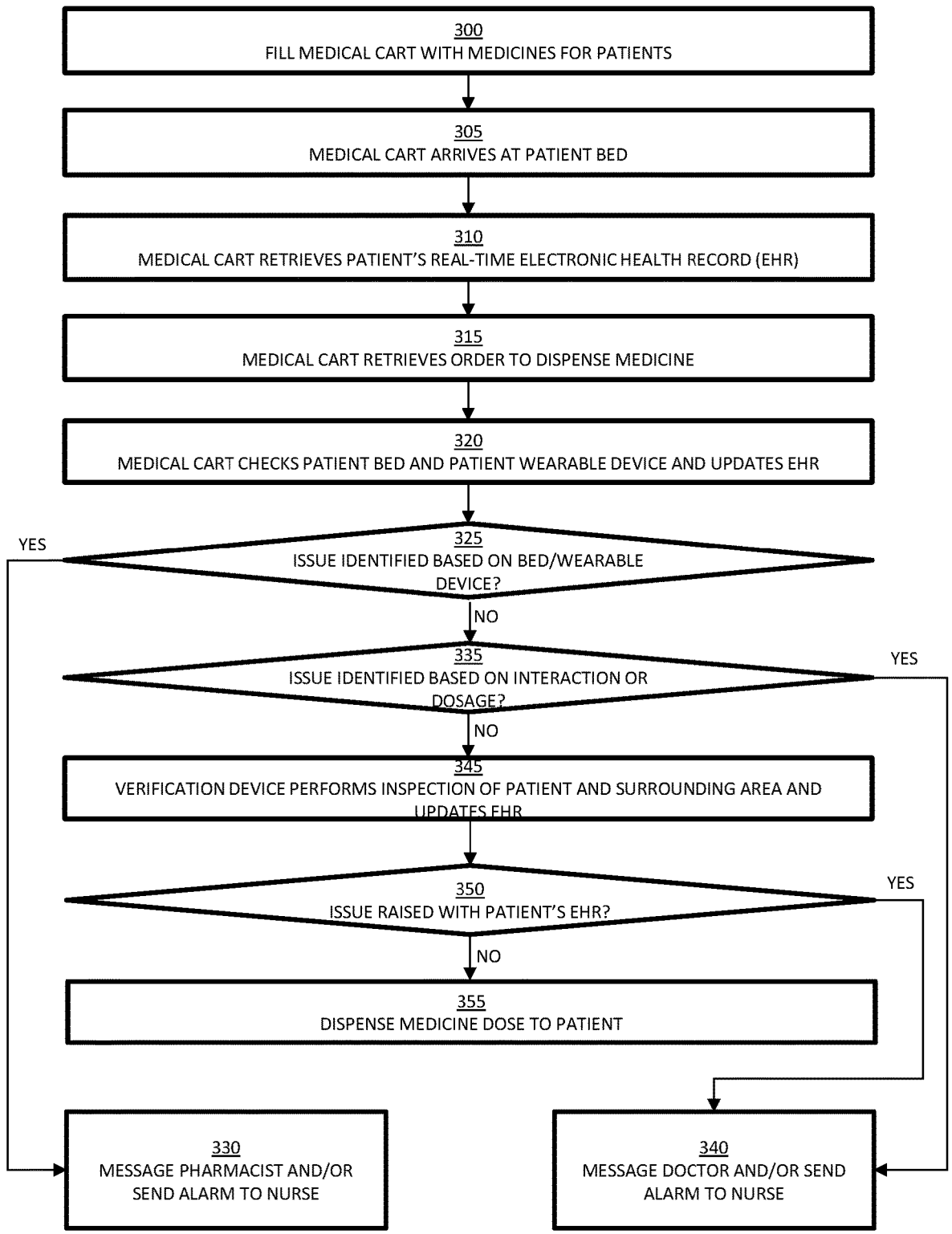
FIG. 3 depicts a flowchart of an exemplary method performed in accordance with aspects of the disclosure.

FIG. 3 depicts a flowchart of an exemplary method for medicine disposition in hospitals that is performed by the medicine disposition program module 210 of the computer server 205 and/or the medical cart program module 230 of the medical cart 225 in accordance with aspects of the disclosure. The steps of the method may be performed in the environment of FIG. 2 and are described with reference to the elements shown in FIG. 2.

At step 300, the medical cart 225 is filled with medicines for patients. In embodiments, step 300 comprises a pharmacist in a hospital pharmacy filling prescriptions entered in or transmitted to the pharmacy computer system 220 (e.g., by doctors) and placing the filled prescriptions in a locking cabinet, drawer, or shelf of the medical cart 225. In embodiments, the prescriptions are dispensed by the pharmacist into intelligent medicine bottles that include RFID tags that are readable by the medical cart 225 to identify the medicine stored therein and the intended patient. Additionally, in embodiments, at step 300, the medical cart program module 230 of the medical cart 225 retrieves prescription information (i.e., orders to dispense a medicine) from the pharmacy computer system 220, including patient identification information, patient location information, medicine name, dosage, and dosing instructions, either directly or via the medicine disposition program module 210 of the computer server 205.

Still referring to FIG. 3, at step 305, the medical cart 225 arrives at a patient bed 240. In embodiments, step 305 comprises the medical cart program module 230 of the medical cart 225 retrieving patient identification information and patient location information stored at step 300 and causing the medical cart 225 to autonomously or semi-autonomously travel to the hospital room indicated by the patient location information and arrive at the patient bed 240 of the patient indicated by the patient identification information. In embodiments, the medical cart program module 230 of the medical cart 225 communicates with the patient wearable device 235 and/or the patient bed 240 to receive identification information for the patient and verifies the identity of the patient based on the received identification information, thereby confirming that the medical cart 225 has arrived at the correct patient bed 240.

Still referring to FIG. 3, at step 310, the medical cart 225 retrieves a patient's real-time EHR. In embodiments, step 310 comprises the medical cart program module 230 of the medical cart 225 retrieving the patient's real-time EHR from the EHR system 215, either directly or via the medicine disposition program module 210 of the computer server 205.

Still referring to FIG. 3, at step 315, the medical cart 225 retrieves an order to dispense a medicine. In embodiments, step 315 comprises the medical cart program module 230 of the medical cart 225 retrieving the order to dispense the medicine, received at step 300, corresponding to the patient in the patient bed 240 at which the medical cart 225 arrived at step 305.

Still referring to FIG. 3, at step 320, the medical cart 225 checks the patient bed 240 and the patient wearable device 235 and updates the patient's EHR. In embodiments, step 320 comprises the medical cart program module 230 of the medical cart 225 receiving data collected by the patient bed 240 using one or more sensors such as digital video cameras, digital still cameras, microphones, temperature sensors, motion sensors, location sensors, and any other type of digital sensor that collects data about the patient and/or an environment (e.g., a hospital room) in which the patient bed 240 is located. Additionally, in embodiments, step 320 comprises the medical cart program module 230 of the medical cart 225 receiving data collected by the patient wearable device 235 (e.g., biometric data and/or health data) and/or data stored on the patient wearable device 235, including information about medicines, allergies, and other medical records.

Still referring to step 320, in embodiments, the data received by the medical cart program module 230 of the medical cart 235 from the patient bed 240 and the patient wearable device 235 is used by the medical cart program module 230 and/or the medicine disposition program module 210 of the computer server 205 to determine information about the patient's current health status (e.g., blood sugar level). In embodiments, the medical cart program module 230 and/or the medicine disposition program module 210 of the computer server 205 sends a request to the EHR system 215 to update the patient's EHR in real-time based on the data received by the medical cart program module 230 of the medical cart 235 from the patient bed 240 and the patient wearable device 235 (including information about medicines, allergies, and other medical records) and the determined information about the patient's current health status.

Still referring to FIG. 3, at step 325, the medical cart 225 determines whether or not an issue is identified based on the information from the patient bed 240 and the patient wearable device 235. In embodiments, step 320 comprises the medical cart program module 230 of the medical cart 225 and/or the medicine disposition program module 210 of the computer server 205 determining whether or not a health concern is identified based on the information from the patient bed 240 and the patient wearable device 235. In embodiments, the medical cart program module 230 of the medical cart 225 and/or the medicine disposition program module 210 of the computer server 205 analyzes the data received by the medical cart program module 230 of the medical cart 235 from the patient bed 240 and the patient wearable device 235 collected at step 320 to determine whether or not a health concern exists. In other embodiments, the EHR system 215 determines whether or not a health concern exists based on the request to the EHR system 215 to update the patient's EHR at step 320. If the medical cart program module 230 of the medical cart 225 and/or the medicine disposition program module 210 of the computer server 205 identifies a health concern, then the flow proceeds to step 330. On the other hand, if the medical cart program module 230 of the medical cart 225 and/or the medicine disposition program module 210 of the computer server 205 does not identify a health concern, then the flow proceeds to step 335.

Still referring to FIG. 3, at step 330, the medical cart 225 messages the pharmacist and/or sends an alarm to a nurse via a hospital social network application (e.g., a social media application that is installed on mobile devices of pharmacists, nurses, and doctors at a hospital). In embodiments, step 330 comprises the medical cart program module 230 of the medical cart 225 and/or the medicine disposition program module 210 of the computer server 205 sending a message to the pharmacist and/or sending the alarm to the nurse via the hospital social network application in response to the health concern being identified at step 325.

Still referring to FIG. 3, at step 335, the medical cart 225 determines whether or not an issue is identified based on a medicine interaction and/or a medicine dosage. In embodiments, step 335 comprises the medical cart program module 230 of the medical cart 225 and/or the medicine disposition program module 210 of the computer server 205 determining whether or not an issue is identified based on a medicine interaction and/or a medicine dosage. In embodiments, the medical cart program module 230 of the medical cart 225 and/or the medicine disposition program module 210 of the computer server 205 retrieves the patient's EHR from the EHR system 215, compares the patient's current medicines as identified in the EHR with the prescription information received at step 300, and determines whether or not there is an adverse interaction between the current medicines and a medicine and/or dosage indicated in the prescription information. Additionally, in embodiments, the medical cart program module 230 of the medical cart 225 and/or the medicine disposition program module 210 of the computer server 205 retrieves drug allergy information from the patient wearable device 235 and determines whether or not there is a drug allergy issue with the medicine identified in the prescription information received at step 300. If the medical cart program module 230 of the medical cart 225 and/or the medicine disposition program module 210 of the computer server 205 identifies an adverse interaction and/or a drug allergy issue, then the flow proceeds to step 340. On the other hand, if the medical cart program module 230 of the medical cart 225 and/or the medicine disposition program module 210 of the computer server 205 does not identify an adverse interaction and/or a drug allergy issue, then the flow proceeds to step 345.

Still referring to FIG. 3, at step 340, the medical cart 225 messages the doctor and/or sends an alarm to a nurse via the hospital social network application (e.g., the social media application that is installed on mobile devices of pharmacists, nurses, and doctors at the hospital). In embodiments, step 340 comprises the medical cart program module 230 of the medical cart 225 and/or the medicine disposition program module 210 of the computer server 205 sending a message to the doctor and/or sending the alarm to the nurse via the hospital social network application in response to an adverse interaction and/or a drug allergy issue being identified at step 335.

Still referring to FIG. 3, at step 345, the medical cart 225 causes the verification device 250 to perform an inspection of the patient and surrounding area and update the EHR. In embodiments, step 345 comprises the medical cart program module 230 of the medical cart 225 and/or the medicine disposition program module 210 of the computer server 205 causing the verification device 250 to perform the inspection of the patient and surrounding area (e.g., the hospital room), using digital video cameras, digital still cameras, microphones, temperature sensors, motion sensors, location sensors, and any other type of digital sensor included in the verification device 250.

Still referring to step 345, in embodiments, in response to the verification device 250 performing the inspection of the patient and surrounding area, the medical cart program module 230 of the medical cart 225 and/or the medicine disposition program module 210 of the computer server 205 receives data from the digital video cameras, digital still cameras, microphones, temperature sensors, motion sensors, location sensors, and any other type of digital sensor included in the verification device 250. Additionally, in embodiment, step 345 comprises the medical cart program module 230 of the medical cart 225 and/or the medicine disposition program module 210 of the computer server 205 receiving information from the real-time measuring devices 245 regarding current medical characteristics of the patient (e.g., pulse, blood pressure, blood oxygen saturation, respiration rate, etc.). The medical cart program module 230 of the medical cart 225 and/or the medicine disposition program module 210 of the computer server 205 analyzes this data to determine information about the patient's current health status (e.g., pain levels based on visual cues, low blood pressure, etc.). In embodiments, the medical cart program module 230 and/or the medicine disposition program module 210 of the computer server 205 sends a request to the EHR system 215 to update the patient's EHR in real-time based on the data received by the medical cart program module 230 of the medical cart 235 from the verification device 250 and the determined information about the patient's current health status.

Still referring to FIG. 3, at step 350, the medical cart 225 determines whether or not an issue is raised with the patient's EHR. In embodiments, step 350 comprises the medical cart program module 230 of the medical cart 225 and/or the medicine disposition program module 210 of the computer server 205 determining whether or not a health concern exists (e.g., high pain levels, low blood pressure when medicine to dispense is for high blood pressure, etc.) based on the EHR which was updated at step 345. In embodiments, the medical cart program module 230 of the medical cart 225 and/or the medicine disposition program module 210 of the computer server 205 analyzes the updated EHR to determine whether or not a health concern exists. In other embodiments, the EHR system 215 determines whether or not a health concern exists based on the request to the EHR system 215 to update the patient's EHR at step 345. If the medical cart program module 230 of the medical cart 225 and/or the medicine disposition program module 210 of the computer server 205 identifies a health concern, then the flow proceeds to step 340. On the other hand, if the medical cart program module 230 of the medical cart 225 and/or the medicine disposition program module 210 of the computer server 205 does not identify a health concern, then the flow proceeds to step 355.

Still referring to FIG. 3, at step 355, the medical cart 225 dispenses the medicine dose to the patient. In embodiments, step 355 comprises the medical cart program module 230 of the medical cart 225 and/or the medicine disposition program module 210 of the computer server 205 dispensing the medicine dose to the patient. In embodiments, the medical cart program module 230 of the medical cart 225 dispenses the medicine dose specified in the prescription information associated with the patient received at step 300. In embodiments, in the dispensing the medicine, the medical cart program module 230 of the medical cart 225 verifies that the proper medicine and dose is being dispensed based on the RFID tag on the intelligent medicine bottle. Additionally, in embodiments, in the dispensing the medicine, the medical cart program module 230 of the medical cart 225, in conjunction with the verification device 250, verifies that the proper medicine and dose is being dispensed based on a comparison of size, shape, and color of a pill to an expected size, shape, color, and/or weight. In embodiments, after verifying that the proper medicine and dose is being dispensed, the medical cart program module 230 of the medical cart 225 dispenses the medicine dose to the patient by unlocking the locking cabinet, drawer, or shelf of the medical cart 225 containing the medicine that was placed in the medical cart 225 at step 300.

In embodiments, a service provider could offer to perform the processes described herein. In this case, the service provider can create, maintain, deploy, support, etc., the computer infrastructure that performs the process operations of the disclosure for one or more customers. These customers may be, for example, any business that uses cloud computing technology. In return, the service provider can receive payment from the customer(s) under a subscription and/or fee agreement and/or the service provider can receive payment from the sale of advertising content to one or more third parties.

In still additional embodiments, embodiments provide a computer-implemented method, via a network. In this case, a computer infrastructure, such as computer system/server 12 (FIG. 1), can be provided and one or more systems for performing the processes of the disclosure can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the disclosure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving, by a computing device via a computer network, an electronic health record (EHR) of a patient from an EHR computer system;
receiving, by the computing device via the computer network, an order to dispense a medicine to the patient;

receiving, by the computing device via the computer network, real-time information from a wearable Internet of Things (IoT) device of the patient and updating the EHR of the patient based on the real-time information from the wearable IoT device of the patient, wherein the real-time information from the wearable IoT device of the patient comprises biometric data, health data, and real-time information about medicines, allergies, medical records, current vitals, allergy warnings, activity, and fitness of the patient, from databases attached to IoT devices and from real-time sensor readings;

determining, by the computing device, that a health concern is not identified based on the real-time information from the wearable IoT device of the patient; and dispensing, by the computing device, the medicine to the patient in accordance with the order and based on the determining, by the computing device, that a health concern is not identified based on the real-time information from the wearable IoT device of the patient.

2. The method according to claim 1, wherein the medicine is contained in an intelligent medicine bottle that includes a radio frequency identification (RFID) tag that identifies the medicine contained in the intelligent medicine bottle, wherein the dispensing the medicine comprises verifying that the medicine matches the order using the RFID tag on the intelligent medicine bottle.

3. The method according to claim 1, wherein the dispensing the medicine comprises verifying that the medicine matches a proper medicine and dose based on a comparison of size, shape, and color of a pill to an expected size, shape, and color, the method further comprising unlocking a locking compartment of a medical cart containing the medicine based on the verifying that the medicine matches the proper medicine and dose.

4. The method according to claim 1, further comprising storing profiles for each of a pharmacy computer system, a medical cart, the wearable IoT device of the patient, a patient IoT bed, real-time measuring devices, and a verification device; and using the profiles to verify integrity and consistency of data received from the pharmacy computer system, the medical cart, the wearable IoT device of the patient, the patient IoT bed, the real-time measuring devices, and the verification device.

5. The method according to claim 1, further comprising receiving, by the computing device, data from a digital video camera and determining a current health status of the patient based on the data from the digital video camera.

6. The method according to claim 5, further comprising receiving, by the computing device, data from measuring devices including pulse, blood pressure, blood oxygen saturation, and respiration rate, and wherein the data from the measuring devices are used in the determining the current health status of the patient, and wherein the real-time information from the wearable IoT device of the patient further comprises real-time information about medicine allergies, medicines with interactions, and medicines which adversely react with the patient.

7. The method according to claim 1, wherein the IoT devices comprise an IoT bed of the patient, the method further comprising receiving, by the computing device, real-time information from the IoT bed of the patient and updating the EHR of the patient based on the real-time information from the IoT bed of the patient, and wherein the determining that the health concern is not identified is further based on both the information from the wearable IoT device and the real-time information from the IoT bed of the patient.

8. A computer program product comprising one or more computer readable storage media having program instructions collectively stored on the one or more computer readable storage media, the program instructions executable to:

receive, via a computer network, an electronic health record (EHR) of a patient from an EHR computer system;

receive, via the computer network, an order to dispense a medicine to the patient;

receive, via the computer network, real-time information from a wearable Internet of Things (IoT) device of the patient and update the EHR of the patient based on the real-time information from the wearable IoT device of the patient, wherein the real-time information from the wearable IoT device of the patient comprises biometric data, health data, and real-time information about medicines, allergies, medical records, current vitals, allergy warnings, activity, and fitness of the patient, from databases attached to IoT devices and from real-time sensor readings;

determine that a health concern is not identified based on the real-time information from the wearable IoT device of the patient;

receive real-time data from a digital video camera and determine a current health status of the patient based on the real-time data from the digital video camera; and update the EHR of the patient based on the determined current health status of the patient and based on the determining that a health concern is not identified based on the real-time information from the wearable IoT device of the patient.

9. The computer program product according to claim 8, the program instructions further being executable to:

store profiles for each of a pharmacy computer system, a medical cart, the wearable IoT device of the patient, a patient Internet of Things (IoT) bed, real-time measuring devices, and a verification device; and using the profiles to verify integrity and consistency of data received from the pharmacy computer system, the medical cart, the wearable IoT device of the patient, the patient IoT bed, the real-time measuring devices, and the verification device.

10. The computer program product according to claim 8, the program instructions further being executable to:

determine that an interaction issue with the medicine is not identified based on the EHR of the patient; and dispense the medicine to the patient in accordance with the order.

11. The computer program product according to claim 8, the program instructions further being executable to receive data regarding current medical characteristics of the patient, determine a current health status of the patient based on the data, and update the EHR of the patient based on the data and the current health status of the patient.

12. The computer program product according to claim 11, the program instructions further being executable to:

determine that the health concern exists based on the updated EHR; and send a message to a doctor regarding the health concern.

13. The computer program product according to claim 11, the program instructions further being executable to:
- determine that the health concern is not identified based on the updated EHR; and
- dispense the medicine to the patient in accordance with the order.

14. A system comprising:
a processor, a computer readable memory, one or more computer readable storage media, and program instructions collectively stored on the one or more computer readable storage media, the program instructions executable to:
- receive, via a computer network, an electronic health record (EHR) of a patient from an EHR computer system;
- receive, via the computer network, an order to dispense a medicine to the patient;
- receive, via the computer network, real-time information from a wearable Internet of Things (IoT) device of the patient and update the EHR of the patient based on the real-time information from the wearable IoT device of the patient, wherein the real-time information from the wearable IoT device of the patient comprises biometric data, health data, and real-time information about medicines, allergies, medical records, current vitals, allergy warnings, activity, and fitness of the patient, from databases attached to IoT devices and from real-time sensor readings;
- determine that a health concern is not identified based on the real-time information from the wearable IoT device of the patient; and
- dispense the medicine to the patient in accordance with the order and based on the determining, by the computing device, that a health concern is not identified based on the real-time information from the wearable IoT device of the patient.

15. The system according to claim 14, wherein the medicine is contained in an intelligent medicine bottle that includes a radio frequency identification (RFID) tag that identifies the medicine contained in the intelligent medicine bottle, wherein the dispensing the medicine comprises verifying that the medicine matches the order using the RFID tag on the intelligent medicine bottle.

16. The system according to claim 15, wherein the dispensing the medicine comprises verifying that the medicine matches a proper medicine and dose based on a comparison of size, shape, and color of a pill to an expected size, shape, and color,
the method further comprising unlocking a locking compartment of a medical cart containing the medicine based on the verifying that the medicine matches the proper medicine and dose.

17. The system according to claim 14, the program instructions further being executable to store profiles for each of a pharmacy computer system, a medical cart, the wearable IoT device of the patient, a patient Internet of Things (IoT) bed, real-time measuring devices, and a verification device; and
use the profiles to verify integrity and consistency of data received from the pharmacy computer system, the medical cart, the wearable IoT device of the patient, the patient IoT bed, the real-time measuring devices, and the verification device.

18. The system according to claim 14, the program instructions further being executable to receive data from a digital video camera and determine a current health status of the patient based on the data from the digital video camera.

19. The system according to claim 18, the program instructions further being executable to receive data from measuring devices including pulse, blood pressure, blood oxygen saturation, and respiration rate, and
wherein the data from the measuring devices is used in the determining the current health status of the patient.

20. The system according to claim 14, wherein the IoT devices comprise an IoT bed of the patient, the program instructions further being executable to receive real-time information from the IoT bed of the patient and update the EHR of the patient based on the real-time information from the IoT bed of the patient, and
wherein the determining that the health concern is not identified is further based on both the information from the wearable IoT device and the real-time information from the IoT bed of the patient.

* * * * *